US009922415B2

(12) United States Patent
Inoue et al.

(10) Patent No.: US 9,922,415 B2
(45) Date of Patent: Mar. 20, 2018

(54) INSPECTION METHOD, INSPECTION APPARATUS, AND INSPECTION SYSTEM

(71) Applicant: NuFlare Technology, Inc., Yokohama-shi (JP)

(72) Inventors: Takafumi Inoue, Chigasaki (JP); Nobutaka Kikuiri, Koganei (JP); Hiroteru Akiyama, Yokohama (JP)

(73) Assignee: NuFlare Technology, Inc., Yokohama-shi (JP)

( * ) Notice: Subject to any disclaimer, the term of this patent is extended or adjusted under 35 U.S.C. 154(b) by 45 days.

(21) Appl. No.: 15/071,339

(22) Filed: Mar. 16, 2016

(65) Prior Publication Data
US 2016/0292839 A1 Oct. 6, 2016

(30) Foreign Application Priority Data

Apr. 1, 2015 (JP) ................................. 2015-075259

(51) Int. Cl.
G06K 9/00 (2006.01)
G06T 7/00 (2017.01)
G01N 21/956 (2006.01)

(52) U.S. Cl.
CPC ........... G06T 7/001 (2013.01); G01N 21/956 (2013.01); G01N 21/95607 (2013.01); G06T 2207/30148 (2013.01)

(58) Field of Classification Search
CPC ............ G01N 21/956; G01N 21/95607; G06T 2207/30148; G06T 7/001
See application file for complete search history.

(56) References Cited

U.S. PATENT DOCUMENTS

2008/0317329 A1* 12/2008 Shibuya ................ G06T 7/0004
382/149
2012/0026316 A1* 2/2012 Nagahama ....... G01N 21/95607
348/92
2015/0369752 A1* 12/2015 Honda ................ G01N 21/8851
356/237.2

FOREIGN PATENT DOCUMENTS

JP 2009-229230 10/2009

* cited by examiner

Primary Examiner — Phuoc Tran
(74) Attorney, Agent, or Firm — Oblon, McClelland, Maier & Neustadt, L.L.P.

(57) ABSTRACT

An inspection method includes: irradiating a first portion of a sample to be inspected with a lighting light; obtaining a first optical image in which the lighting light transmitted through the first portion is imaged or a second optical image in which the lighting light reflected by the first optical image is imaged; based on a first defect determination threshold, performing a first comparison between a first reference image referred to the first optical image and the first optical image or a second comparison between a second reference image referred to the second optical image and the second optical image; determining whether the first portion includes a first defect; storing a first coordinate of the first defect, the first defect determination threshold, the first optical image or the second optical image, and the first reference image or the second reference image in a case where the first portion is determined to have the first defect; calculating the number of first defects in the first portion as a defect total number; calculating a second defect determination threshold increased by a predetermined amount from the first defect determination threshold in a case where the defect total number is larger than the defect number threshold; and equalizing the second defect determination threshold with the first defect determination threshold in a case where the (Continued)

defect total number is equal to or less than the defect number threshold.

11 Claims, 4 Drawing Sheets

INSPECTION METHOD, INSPECTION APPARATUS, AND INSPECTION SYSTEM

CROSS-REFERENCE TO RELATED APPLICATION

This application is based upon and claims the benefit of priority from Japanese Patent Applications No. 2015-075259, filed on Apr. 1, 2015, the entire contents of which are incorporated herein by reference.

FIELD OF THE INVENTION

Embodiments described herein relate generally to an inspection method, an inspection apparatus, and an inspection system. For example, the embodiment relates to an inspection apparatus, an inspection system, and an inspection method for inspecting a pattern by obtaining an optical image of a pattern image by irradiating a sample to be inspected, such as a mask used to manufacture a semiconductor device, with a laser light.

BACKGROUND OF THE INVENTION

Accuracy control of a circuit line width required in a semiconductor device is increasingly required in recent years. Such a semiconductor device is manufactured by forming a circuit by exposing and transferring a pattern on a wafer by a reduced projection exposure apparatus called a stepper by using an original pattern (called a photolithography mask or a reticle, and hereinafter collectively called a mask) in which a circuit pattern is formed. Therefore, a mask for transferring a fine circuit pattern on a wafer is manufactured by using a pattern drawing apparatus using an electron beam. The pattern drawing apparatus can draw a fine circuit pattern. The pattern circuit apparatus can directly draw a pattern circuit on a wafer.

Improvement of yield is essential in manufacturing of LSI, such as a central processing unit (CPU) and a field programmable gate array (FPGA), requiring a high manufacturing cost. One of significant factors to reduce yield is a pattern defect of a mask used to expose and transfer an ultra fine pattern on a semiconductor wafer by a photolithography technique. In recent years, as the size of an LSI pattern formed on a semiconductor wafer is miniaturized, a size to be detected as a pattern defect is significantly reduced. Therefore, a highly accurate pattern inspection apparatus to inspect a defect of a transfer mask used in LSI manufacturing is desirable.

An inspection method is known in which an optical image, in which a pattern formed on a sample of such as a photolithography mask is imaged at a predetermined magnification by using an expansion optical system is compared with design data or an optical image, in which the same pattern on the sample is imaged. Examples of a pattern inspection method include a "die-to-die inspection" and a "die-to-database inspection". In the die-to-die inspection, data of optical images, in which the same patterns at different locations on the same mask are imaged, are compared each other. In the die-to-database inspection, drawing data (pattern data), in which pattern-designed CAD data is converted into an apparatus input format to be input by a drawing apparatus when a pattern is drawn to a mask, is input to an inspection apparatus, design image data (a reference image) is generated based on the drawing data, and the design image data and an optical image formed by the pattern and being measurement data are compared. In an inspection method in such an inspection apparatus, a sample is arranged on a stage and inspected by which a beam scans on the sample when the stage is moved. The sample is irradiated with the beam by a light source and a lighting optical system. A light transmitted through or reflected by the sample is imaged on a light detector via the optical system. An image formed by the light detector is sent to a comparison circuit as measurement data. In the comparison circuit, after images are positioned each other, measurement data and reference data are compared in accordance with an appropriate algorithm. In the case of nonconformity, it is determined that there is a defective pattern.

SUMMARY OF THE INVENTION

An inspection method according to an embodiment described herein includes: irradiating a first portion of a sample to be inspected with a lighting light; obtaining a first optical image in which the lighting light transmitted through the first portion is imaged or a second optical image in which the lighting light reflected by the first optical image is imaged; based on a first defect determination threshold, performing a first comparison between a first reference image and the first optical image or a second comparison between a second reference image and the second optical image; determining whether the first portion includes a first defect; storing a first coordinate of the first defect, the first defect determination threshold, the first optical image or the second optical image, and the first reference image or the second reference image in the case where the first portion is determined to have the first defect; calculating the number of first defects in the first portion as a defect total number; calculating a second defect determination threshold increased by a predetermined amount from the first defect determination threshold in the case where the defect total number is larger than the defect number threshold; and equalizing the second defect determination threshold with the first defect determination threshold in the case where the defect total number is equal to or less than the defect number threshold.

An inspection apparatus according to the embodiment includes an irradiation circuit, an imaging circuit, a comparison circuit, a determination circuit, a defect determination threshold storage device, a defect information storage device, a defect total number storage device, and a defect number threshold storage device. The irradiation circuit irradiates a first portion of a sample to be inspected with a lighting light. The imaging circuit obtains a first optical image in which the lighting light transmitted through the first portion is imaged or a second optical image in which the lighting light reflected by the first portion is imaged. The comparison circuit performs, based on a first defect determination threshold, a first comparison between a first reference image referred to the first optical image and the first optical image or a second comparison between a second reference image referred to the second optical image and the second optical image. The determination circuit determines whether the first portion includes a first defect. The defect determination threshold storage device stores the first defect determination threshold. The defect information storage device stores a first coordinate of the first defect, the first defect determination threshold, the first optical image or the second optical image, and the first reference image or the second reference image. The defect total number storage device stores the number of first defects in the first portion as a defect total number. The defect number threshold storage device stores a defect number threshold.

DETAILED DESCRIPTION OF THE EMBODIMENTS

An embodiment will be described below with reference to the drawings.

Hereinafter, a photolithography mask (a sample to be inspected) will be simply called a mask.

Embodiment

An inspection method according to an embodiment described herein includes: irradiating a first portion of a sample to be inspected with a lighting light; obtaining a first optical image in which the lighting light transmitted through the first portion is imaged or a second optical image in which the lighting light reflected by the first optical image is imaged; based on a first defect determination threshold, performing a first comparison between a first reference image referred to the first optical image and the first optical image or a second comparison between a second reference image referred to the second optical image and the second optical image; determining whether the first portion includes a first defect; storing a first coordinate of the first defect, the first defect determination threshold, the first optical image or the second optical image, and the first reference image or the second reference image in the case where the first portion is determined to have the first defect; calculating the number of first defects in the first portion as a defect total number; calculating a second defect determination threshold increased by a predetermined amount from the first defect determination threshold in the case where the defect total number is larger than the defect number threshold; and equalizing the second defect determination threshold with the first defect determination threshold in the case where the defect total number is equal to or less than the defect number threshold.

Figure 1:
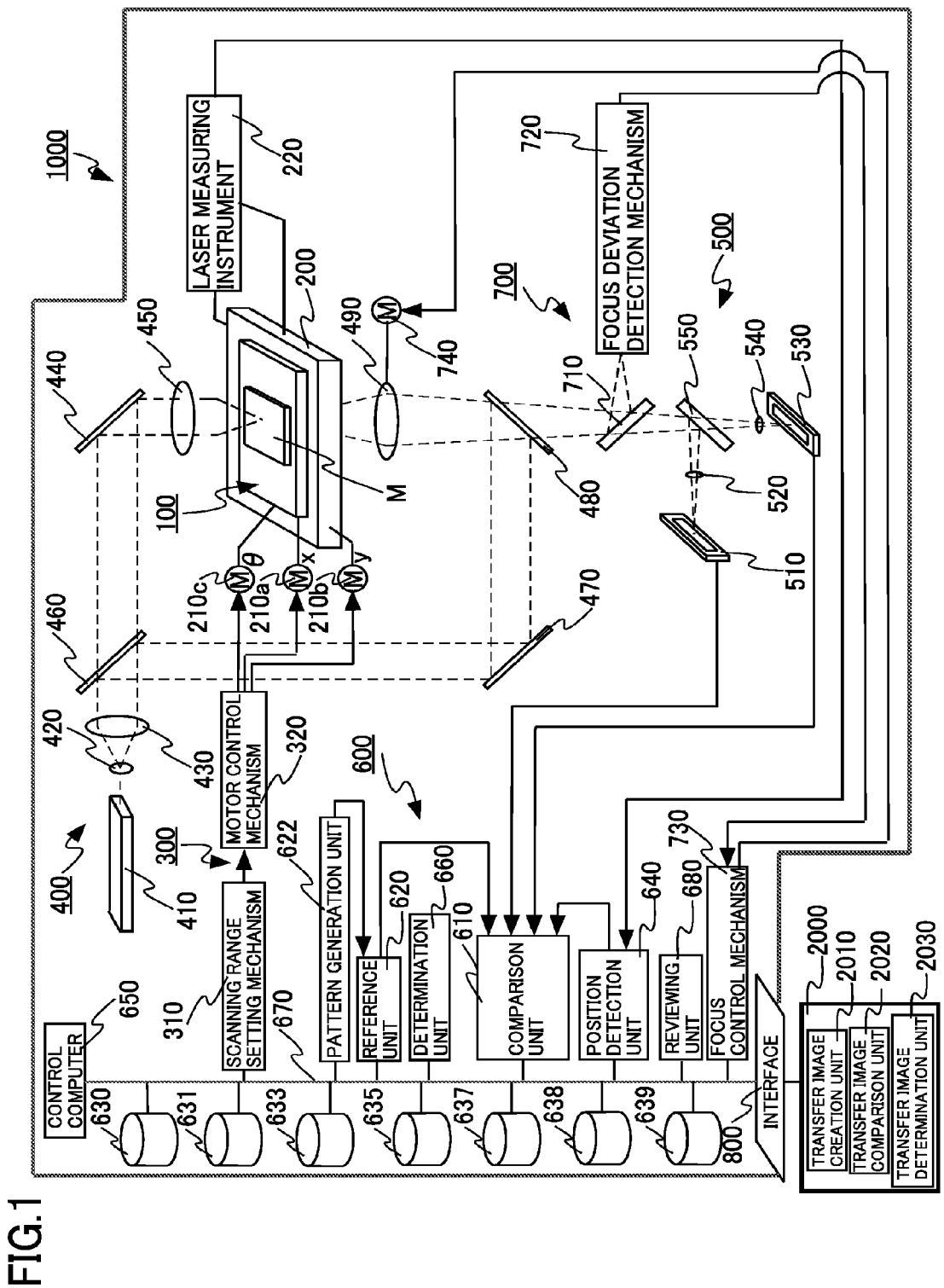
FIG. 1 is a schematic view of a main portion of an inspection apparatus and a lithography simulator according to an embodiment described herein.

FIG. 1 is a schematic view of an inspection apparatus 1000 and a lithography simulator 2000 according to the embodiment. The inspection apparatus according to the embodiment is a pattern inspection apparatus to inspect a defect in a mask.

A mask M is arranged in a storage 100.

A stage 200 is disposed under the storage 100 and supports the storage 100. The stage 200 is moved in an X direction and a Y direction, which are mutually orthogonal horizontal directions, by a first motor 210a and a second motor 210b. Further, the stage 200 is rotated by a third motor 210c on a surface perpendicular in a vertical direction. A laser measuring instrument 220 measures positions of the stage 200 in the X direction and in the Y direction.

A moving control unit 300 includes a scanning range setting mechanism 310 and a motor control mechanism 320. The scanning range setting mechanism 310 is connected to a control computer 650 to be described later via a bus line 670. The motor control mechanism 320 controls the first motor 210a, the second motor 210b, and the third motor 210c such that the stage 200 is moved within a scanning range set by the scanning range setting mechanism 310.

A lighting unit 400 includes a light source 410, a lens 420 for a first lighting unit, a lens 430 for a second lighting unit, a mirror 440 for the first lighting unit, a condenser lens 450, a beam distribution unit 460 for the first lighting unit, and a mirror 470 for the second lighting unit, a beam distribution unit 480 for the second lighting unit, and an objective lens 490.

A lighting light such as a laser light emitted from the light source 410 is expanded so as to become a parallel beam by the lens 420 for the first lighting unit and the lens 430 for the second lighting unit. The mirror 440 for the first lighting unit and the condenser lens 450 irradiate an upper surface of the mask M with the expanded beam. The lens 420 for the first lighting unit, the lens 430 for the second lighting unit, the mirror 440 for the first lighting unit, and the condenser lens 450 form a light transmitting system. A wavelength of the light source 410 is preferably similar to a wavelength of a light source included in an exposure apparatus in which the mask M is used, since the mask M can be inspected in a state similar to the state of exposing by using the mask M.

Further, a lighting light such as a laser light emitted from the light source 410 is reflected by the beam distribution unit 460 for the first lighting unit disposed between the lens 430 for the second lighting unit and the mirror 440 for the first lighting unit after the lighting light is expanded so as to become a parallel beam by the lens 420 for the first lighting unit and the lens 430 for the second lighting unit. The mirror 470 for the second lighting unit and the beam distribution unit 480 for the second lighting unit irradiate a lower surface of the mask M with the lighting light reflected by the beam distribution unit 460 for the first lighting unit. A reflection lighting system includes the beam distribution unit 460 for the first lighting unit, the mirror 470 for the second lighting unit, and the beam distribution unit 480 for the second lighting unit. Specifically, a half mirror, a slit, and a polarization beam splitter are preferably used as the beam distribution unit 460 for the first lighting unit and the beam distribution unit 480 for the second lighting unit.

An imaging unit 500 includes a first light detector 510, a lens 520 for a first imaging unit, a second light detector 530, a lens 540 for a second imaging unit, and a separation mirror 550.

A lighting light with which an upper surface of the mask M is irradiated by the light transmitting system and which is transmitted through the mask M is called a transmitted light. A lighting light with which a lower surface of the mask M is irradiated by the reflection lighting system and which is then reflected by the mask M is called a reflected light. The transmitted light and the reflected light enter the separation mirror 550 through the objective lens 490 and the beam distribution unit 480 for the second lighting unit. The transmitted light is imaged by the first light detector 510 through the lens 520 for the first imaging unit from the separation mirror 550. The reflected light is imaged by the second light detector 530 through the lens 540 for the second imaging unit from the separation mirror 550.

A control unit 600 includes a comparison unit 610, a reference unit 620, a pattern generation unit 622, a pattern data storage unit 630, a defect determination threshold storage unit 631, a limit defect determination threshold storage unit 633, a defect number threshold storage unit 635, a defect information storage unit 637, a defect total number storage unit 638, a defect determination algorithm storage unit 639, a position detection unit 640, the control computer 650, a determination unit 660, the bus line 670, and a reviewing unit 680.

An auto focus unit 700 includes an auto focus beam distribution unit 710, a focus deviation detection mechanism 720, a focus control mechanism. 730, and a motor 740 for the auto focus unit.

The reflected light is entered into the focus deviation detection mechanism 720 by the auto focus beam distribution unit 710. The focus deviation detection mechanism 720 detects a focus deviation level from the incident reflected light and inputs the focus deviation level to the focus control mechanism 730. The focus control mechanism 730 moves the objective lens 490 in a height direction by controlling the motor 740 for the auto focus unit based on the input focus deviation level, and the objective lens 490 is focused on the mask M. The stage 200 may be moved in a vertical direction. Specifically, a half mirror, a slit, and a polarization beam splitter are preferably used as the auto focus beam distribution unit 710.

The lithography simulator 2000 includes a transfer image creation unit 2010, a transfer image comparison unit 2020, and a transfer image determination unit 2030. The lithography simulator estimates an exposure image transferred on a wafer from a mask by an exposure apparatus and determines pattern quality on the exposure image. The lithography simulator 2000 is connected to the inspection apparatus 1000 via an interface 800 included in the inspection apparatus 1000. A connection method between the lithography simulator 2000 and the inspection apparatus 1000 is not limited to the above method. For example, the lithography simulator 2000 may be incorporated in the inspection apparatus 1000, and the bus line 670 and the lithography simulator 2000 may be directly connected without the interface 800. An inspection system 3000 includes the inspection apparatus 1000 and the lithography simulator 2000.

Figure 2:
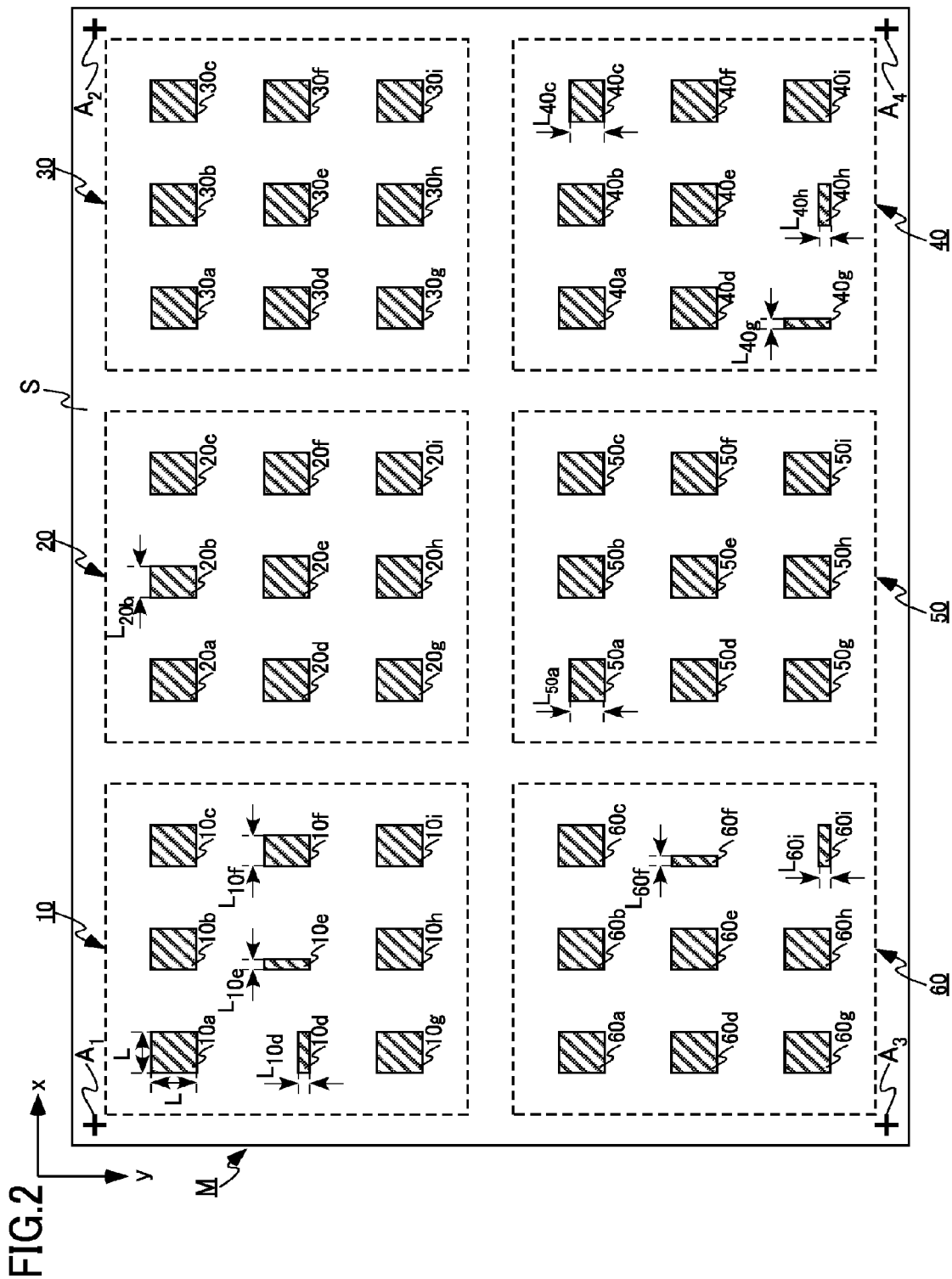
FIG. 2 is a schematic view of a mask inspected in the embodiment.

FIG. 2 is a schematic view of the mask M inspected in the embodiment.

The mask M includes a first portion 10, a second portion 20, a third portion 30, a fourth portion 40, a fifth portion 50, and a sixth portion 60 which are provided on a substrate S. Herein, the substrate S is made of quartz. The first portion 10 includes patterns 10a, 10b, 10c, 10d, 10e, 10f, 10g, 10h, and 10i. The second portion 20 includes patterns 20a, 20b, 20c, 20d, 20e, 20f, 20g, 20h, and 20i. The third portion 30 includes patterns 30a, 30b, 30c, 30d, 30e, 30f, 30g, 30h, and 30i. The fourth portion 40 includes patterns 40a, 40b, 40c, 40d, 40e, 40f, 40g, 40h, and 40i. The fifth portion 50 includes patterns 50a, 50b, 50c, 50d, 50e, 50f, 50g, 50h, and 50i. The sixth portion 60 includes patterns 60a, 60b, 60c, 60d, 60e, 60f, 60g, 60h, and 60i. The patterns are made of, for example, a metal thin film including chrome.

A form of each nondefective pattern is a square, in which the length of one side on a surface parallel to the substrate S is denoted as L. However, the length $L_{10d}$ of one side in a y direction of the pattern 10d is denoted as L/4. The length $L_{10e}$ of one side in an x direction of the pattern 10e is denoted as L/4. The length $L_{10f}$ of one side in an x direction of the pattern 10f is denoted as 3L/4. The length $L_{20b}$ of one side in an x direction of the pattern 20b is denoted as 3L/4. The length $L_{40c}$ of one side in a y direction of the pattern 40c is denoted as 3L/4. The length $L_{40g}$ of one side in an x direction of the pattern 40g is denoted as L/4. The length $L_{40h}$ of one side in a y direction of the pattern 40h is denoted as L/4. The length $L_{50a}$ of one side in a y direction of the pattern 50a is denoted as 3L/4. The length $L_{60f}$ of one side in an x direction of the pattern 60f is denoted as L/4. The length $L_{60i}$ of one side in a y direction of the pattern 60i is denoted as L/4.

As a method for inspecting the mask M, for example, an X axis direction is set to a main scanning direction, and a Y axis direction is set to a sub scanning direction. A lighting light is scanned in the X axis direction by movement of the stage 200 in the X axis direction. A scanning position is moved at a predetermined pitch in the Y axis direction by movement of the stage 200 in the Y axis direction. In the mask M illustrated in FIG. 2, first, the lighting light is scanned in the X axis direction by movement of the stage 200 in the X axis direction, and the first portion 10, the second portion 20, and the third portion 30 are scanned in order. Next, the fourth portion 40 is inspected by moving the stage 200 in the Y axis direction. Next, the lighting light is scanned in the X axis direction by movement of the stage 200 in the X axis direction, and the fifth portion 50 and the sixth portion 60 are inspected in order. However, a method for inspecting the mask M is not limited to the above-described method.

Figure 3:
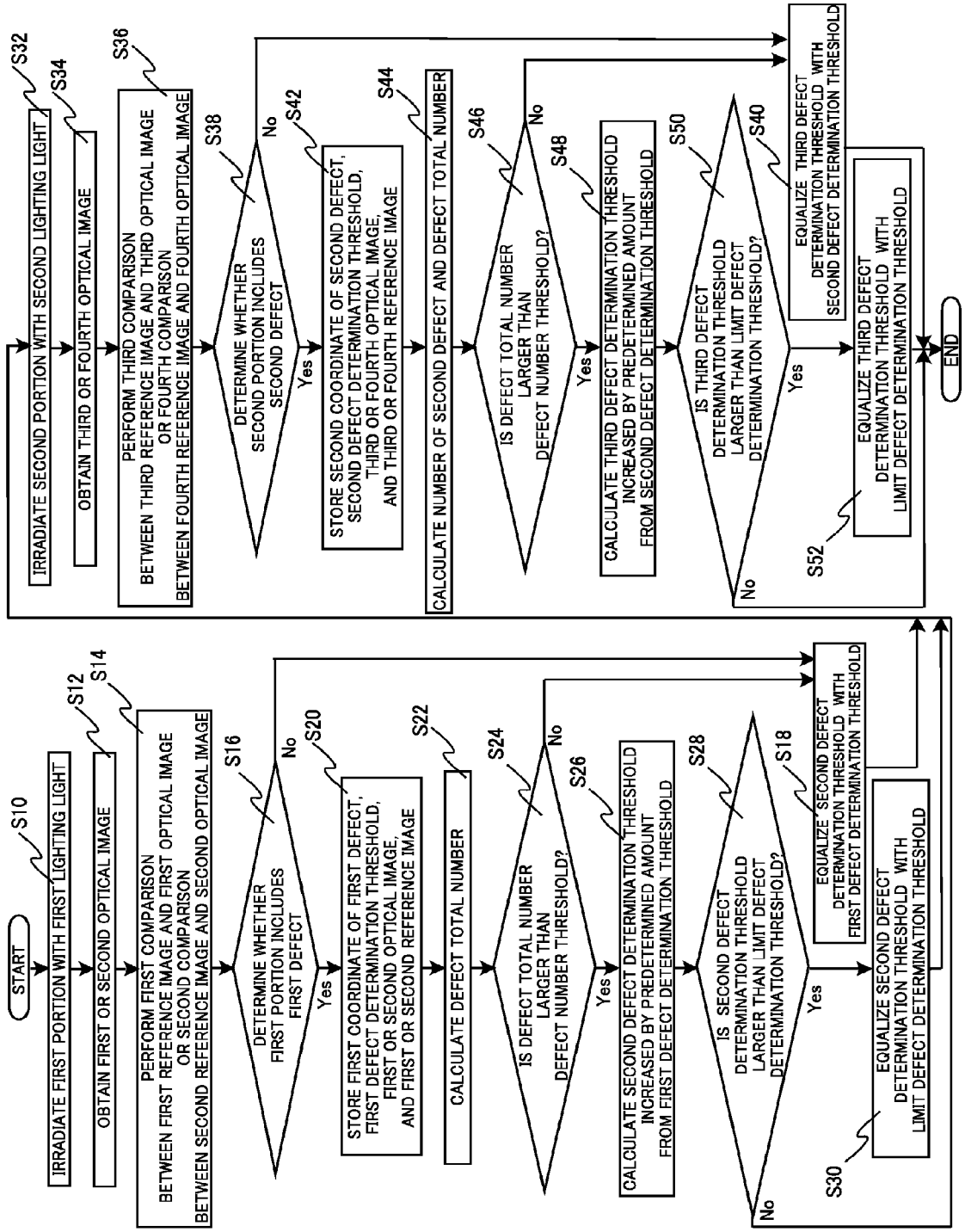
FIG. 3 is a flowchart of an inspection method according to the embodiment.

FIG. 3 is a flowchart of an inspection method according to the embodiment.

First, the control computer 650 irradiates the first portion 10 of the mask M with a lighting light by using the lighting unit 400 (S10). Then, the control computer 650 obtains a transmission optical image or a reflection optical image by using the imaging unit 500 (S12). Lighting lights transmitted through the first portion 10 are imaged in the transmission optical image (hereinafter called a first optical image). Lighting lights reflected by the first portion 10 are imaged in the reflection optical image (hereinafter called a second optical image). The obtained first and second optical images are input to the comparison unit 610.

Next, the control computer 650 inputs pattern data stored in the pattern data storage unit 630 to the pattern generation unit 622 and generates to each layer. The pattern data is preliminarily created by a designer. Herein, the pattern data is generally not designed such that an inspection apparatus 1000 can directly read the data. Therefore, the pattern data is first converted into intermediate data created for each layer, and then converted into data formed so as to be directly read by each inspection apparatus 1000. After that, the pattern data is input to the pattern generation unit 622.

Next, the control computer 650 creates a reference image for transmission (hereinafter called a first reference image) referred to the first optical image, or a reference image for reflection (hereinafter called a second reference image) referred to the second optical image, by using the reference unit 620 from the pattern data generated to each layer in the pattern generation unit 622. The created first or second reference image is input to the comparison unit 610.

Next, the control computer 650 performs a first comparison between the first reference image and the first optical image and (or) performs a second comparison between the second reference image and the second optical image by using the comparison unit 610 based on a first defect determination threshold (S14). An example of the first comparison herein includes a method for comparing an amount of the transmitted light in a pattern portion of the first optical image and an amount of the transmitted light in a pattern portion of the corresponding first reference image. An example of the second comparison herein includes a method for comparing an amount of the reflected light in a pattern portion of the second optical image and an amount of the reflected light in a pattern portion of the corresponding second reference image.

Either of the first optical image and the first reference image or the second optical image and the second reference image and a portion determined to be defective as results of the first comparison and the second comparison are sent to the reviewing unit 680 and reviewed by an operator. Herein, "reviewing" means an operation in which an operator reconfirms a defect portion detected by the inspection apparatus by visually recognizing an optical image and a reference image.

Next, the control computer 650 determines by using the determination unit 660 whether the first portion 10 includes a first defect (S16).

Herein, a defect determination threshold is a threshold for determining whether a pattern to be inspected is defective. The defect determination threshold is stored in the defect determination threshold storage unit 631.

Next, a first defect determination algorithm will be described. Specifically, when the length of one side of a square pattern in a reference image which is not defective is denoted as L, the length of one side of a pattern to be inspected is denoted as $l_0$, and a first defect determination threshold is denoted as $\epsilon_1$, the pattern is determined not to be defective in the case where $|L-l_0|/L<=\epsilon_1$. On the other hand, in the case where $|L-l_0|/L>\epsilon_1$, the pattern is determined to be defective. A defect determination algorithm according to the embodiment is stored in the defect determination algorithm storage unit 639.

If the first defect determination threshold $\epsilon_1$ is 20/100, $|L-l_0|/L=|L-L/4|/L=3/4>20/100$ is established in a y direction of the pattern 10d. Further, $|L-l_0|/L=|L-L/4|=3/4>20/100$ is established in an x direction of the pattern 10e. Further, $|L-l_0|/L=|L-3L/4|=1/4>20/100$ is established in an x direction of the pattern 10f. Therefore, the patterns 10d, 10e, and 10f are determined to be defective. In other words, the first portion 10 is determined to have a first defect.

On the other hand, $|L-l_0|/L=|L-L|/L=0<20/100$ is established in both of x and y directions of the patterns 10a, 10b, 10c, 10g, 10h, and 10i. Therefore, in the first portion 10, the patterns 10a, 10b, 10c, 10g, 10h, and 10i are determined not to be defective.

A defect determination threshold according to the embodiment can be used for defect determination, for example, whereby the above-described first defect determination threshold 20/100 is multiplied by 100 times and set to 20.

As in the embodiment, in the case where the first portion 10 is determined to have the first defect, the control computer 650 stores a first coordinate of the first defect in the first portion 10, a first defect determination threshold, a first or second optical image, a first or second reference image in the defect information storage unit 637 (S20). At this point, defect-related information such as a line width and a form of a defective pattern may be further stored.

Herein, a method for calculating a defect coordinate will be described. A coordinate of a pattern region performing a comparison process at that point is input in the comparison unit 610 from the position detection unit 640. In the case where the determination unit 660 detects a defect, a position coordinate of the defect is calculated as a coordinate correlating to a reference mark in an optical image of the mask M and a defect position. Herein, for example, one of alignment marks $A_1$, $A_2$, $A_3$, and $A_4$ disposed at four corners of an inspection region on the mask M and used in a plate rotation alignment is preferably defined for use as a reference mark. A review screen by the reviewing unit 680 also displays coordinates correlating from the reference mark. In the embodiment, for example, coordinates of the patterns 10d, 10e, and 10f are stored.

Positions of a first or second optical image or a first or second reference image in the mask M may be stored as a coordinate, but this is not limited thereto.

On the other hand, in the case where the first portion 10 is determined not to have a first defect, the control computer 650 equalizes the second defect determination threshold $\epsilon_2$ with the first defect determination threshold $\epsilon_1$=20/100 (S18).

Next, the control computer 650 calculates the number of first defects in the first portion 10 as a defect total number (S22). In the embodiment, the patterns 10d, 10e, and 10f are defective. Therefore, the number of first defects is 3, and the defect total number is 3. The defect total number is stored in the defect total number storage unit 638.

Next, the control computer 650 determines whether a defect total number is larger than a defect number threshold (S24). In the embodiment, the defect number threshold is 2. In this case, since the defect total number is 3, the defect total number is determined to be larger than the defect number threshold. The defect number threshold is stored in the defect number threshold storage unit 635.

If the defect total number is larger than the defect number threshold, the control computer 650 calculates the second defect determination threshold $\epsilon_2$ which is larger than the first defect determination threshold $\epsilon_1$ by a predetermined amount (S26). In the embodiment, the above-described predetermined amount is set to 10/100, and the second defect determination threshold $\epsilon_2$ is calculated by 20/100+10/100=30/100. The above-described predetermined amount and the second defect determination threshold are stored in the defect determination threshold storage unit 631. Further, in the case where the defect total number is larger than the defect number threshold, the control computer 650 may determine to use a defect determination algorithm, which can decrease the number of detected defects in comparison with a first defect determination algorithm, in the second portion 20 as a second defect determination algorithm. A known defect determination algorithm is preferably used as the defect determination algorithm according to the embodiment.

On the other hand, in the case where it is determined that a defect total number is equal to or less than a defect number threshold, the control computer 650 equalizes the second defect determination threshold $\epsilon_2$ with the first defect determination threshold $\epsilon_1$ (S18).

Next, the control computer 650 determines whether the second defect determination threshold $\epsilon_2$ is larger than a limit defect determination threshold (S28). If the second defect determination threshold $\epsilon_2$ is larger than the limit defect determination threshold, the second defect determination threshold is equalized with the limit defect determination threshold (S30). If the second defect determination threshold $\epsilon_2$ is equal to or less than the limit defect determination threshold, the process is moved to S32. In the embodiment, the limit defect determination threshold is 30/100. Then, the second defect determination threshold $\epsilon_2$ is 30/100 which is equal to the limit defect determination threshold. Therefore, the process is moved to S32. The limit defect determination threshold is stored in the limit defect determination threshold storage unit 633.

The defect determination algorithm may determine not to be defective in the case where a defect determination threshold is denoted as $\epsilon_x$ and $L/|L-l_0|>\epsilon_x$ and may determine to be defective in the case where $L/|L-l_0|<=\epsilon_x$. In such a case, for example, in the case where the defect total number is larger than the defect number threshold in S24, the second defect determination threshold which is smaller than the first defect determination threshold by a predetermined amount is calculated in S26. In the case where the defect total number is smaller than the defect number threshold in S24, the second defect determination threshold is equalized with the first defect determination threshold in S18. In addition, for example, the second defect determination threshold is equal to or less than a limit defect determination threshold in S28, the second defect determination threshold is equalized with the limit defect determination threshold in S30.

In the description of S32 to S52 to be described below, descriptions overlapping with the descriptions of S10 to S30 will be omitted.

Next, the control computer 650 irradiates the second portion 20 of the mask M with a lighting light by using the lighting unit 400 (S32). Then, the control computer 650 obtains a transmission optical image or a reflection optical image by using the imaging unit 500 (S34). Lighting lights transmitted through the second portion 20 are imaged in the transmission optical image (hereinafter called a third optical image). Lighting lights reflected by the second portion 20 are imaged in the reflection optical image (hereinafter called a fourth optical image). The obtained third and fourth optical images are input to the comparison unit 610.

Next, by using the reference unit 620, the control computer 650 creates a reference image for transmission (hereinafter called a third reference image) referred to the third optical image, or a reference image for reflection (hereinafter called a fourth reference image) referred to the fourth optical image from pattern data generated to each layer in the pattern generation unit 622. The created third or fourth reference image is input to the comparison unit 610. In the case where the third and fourth reference images are respectively same as the first and second reference image, the third and fourth reference images may not be created.

Next, the control computer 650 performs a third comparison between the third reference image and the third optical image and performs a fourth comparison between the fourth reference image and the fourth optical image by using the comparison unit 610 based on a second defect determination threshold (S36).

Next, the control computer 650 determines by using the determination unit 660 whether the second portion 20 includes a second defect (S38).

In the embodiment, the second defect determination threshold $\epsilon_2$ is 30/100. Further, the second defect determination algorithm and the first defect determination algorithm are the same. Although $l_0=3L/4$ in an x direction of the pattern 20b, $|L-l_0|/L=|L-3L/4|=1/4<30/100$ is established. Therefore, the pattern 20b is determined not to be defective in an x direction. Similarly, the second portion 20 is determined not to be defective.

The first defect determination algorithm and the second defect determination algorithm can be different, for example, in the case where patterns provided in the first portion 10 and the second portion 20 are different, specifically, in the case where a line and space pattern is provided in the first portion 10, and a hole pattern is provided in the second portion 20. Herein, any of defect determination algorithms used for defect determination of known masks can be preferably used for each defect determination algorithm. For example, a defect can be found in the line and space pattern based on an error amount with a true line width or a true line interval. Further, a defect is found in the hole pattern based on an error amount with a true hole size.

In the case where the second portion 20 is determined to have a second defect, the control computer 650 stores a second coordinate of the second defect in the second portion 20, a second defect determination threshold, a third or fourth optical image, a third or fourth reference image in the defect information storage unit 637 (S42). On the other hand, in the case where the second portion 20 is determined not to have the second defect, the control computer 650 equalizes the third defect determination threshold $\epsilon_3$ with the second defect determination threshold $\epsilon_3=30/100$ (S40).

Next, the control computer 650 calculates the number of second defects in the second portion 20. Next, the control computer 650 calculates a defect total number by adding the number of first defects and the number of second defects (S44). Next, the control computer 650 determines whether the defect total number is larger than a defect number threshold (S46). If the defect total number is determined to be larger than the defect number threshold, the control computer 650 calculates the third defect determination threshold $\epsilon_3$ which is increased from the second defect determination threshold $\epsilon_2$ by a predetermined amount (S48). On the other hand, in the case where the defect total number is determined to be smaller than the defect number threshold, the third defect determination threshold $\epsilon_3$ is equalized with the second defect determination threshold $\epsilon_2$ (S40).

Next, the control computer 650 determines whether the third defect determination threshold $\epsilon_3$ is larger than a limit defect determination threshold (S50). If the third defect determination threshold $\epsilon_3$ is larger than the limit defect determination threshold, the third defect determination threshold is equalized with the limit defect determination threshold (S52). The third defect determination threshold $\epsilon_3$ is, for example, used to inspect the third portion 30.

Then, similarly, the third portion 30, the fourth portion 40, the fifth portion 50, and the sixth portion 60 are inspected. The inspection may be finished after the second portion 20 is inspected.

Inspection results in the embodiment are summarized in Table 1.

TABLE 1

|  | First portion | Second portion | Third portion | Fourth portion | Fifth portion | Sixth portion |
| --- | --- | --- | --- | --- | --- | --- |
| Presence or Absence of defect | Present | Absent | Absent | Present | Absent | Present |
| Defect determination threshold | 20/100 | 30/100 | 30/100 | 30/100 | 30/100 | 30/100 |
| Defect total number | 3 | 3 | 3 | 5 | 5 | 7 |

A defect determination threshold is 20/100 in the first portion 10. On the other hand, the defect determination threshold is 30/100 in the second portion 20, the third portion 30, the fourth portion 40, the fifth portion 50, and the sixth portion 60. As this result, a defect total number is 3 in the first portion 10, the second portion 20, and the third portion 30. Further, the defect total number is 5 in the fourth portion 40 and the fifth portion 50. Furthermore, the defect total number is 7 in the sixth portion 60.

A result of an inspection assuming that a defect determination threshold is set to 20/100 in all of the first to sixth is summarized in Table 2.

TABLE 2

|  | First portion | Second portion | Third portion | Fourth portion | Fifth portion | Sixth portion |
|---|---|---|---|---|---|---|
| Presence or Absence of defect | Present | Present | Absent | Present | Present | Present |
| Defect determination threshold | 20/100 | 20/100 | 20/100 | 20/100 | 20/100 | 20/100 |
| Defect total number | 3 | 4 | 4 | 7 | 8 | 10 |

In this case, the second and fifth portions are determined to be defective. Therefore, a defect total number in the sixth portion is 10. Specifically, the defect total number can be decreased by setting defect determination thresholds respectively to 20/100 and 30/100 in the first portion and the second to sixth portions.

Figure 4:
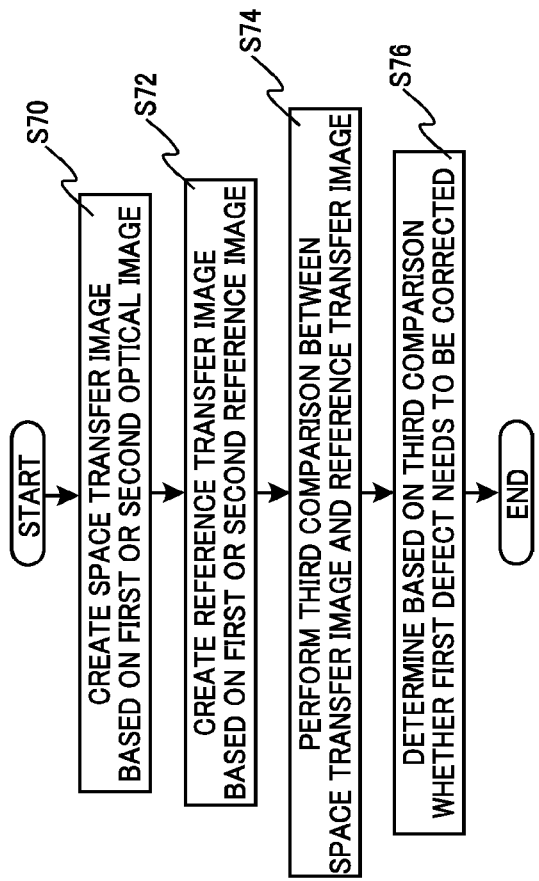
FIG. 4 is a flowchart of an inspection method using the lithography simulator according to the embodiment.

FIG. 4 is a flowchart of the inspection method using a lithography simulator according to the embodiment.

First, the lithography simulator 2000 creates, by using the transfer image creation unit 2010, based on a first or second optical image and a transfer parameter, a space transfer image assuming that the wafer is irradiated with a lightning light for a semiconductor exposure apparatus, and the image is transferred to a wafer. (S70). Herein, the transfer parameter is a kind of a light source used for exposure, such as a positional light source and a dipole light source, a wavelength used for exposure, and the number of lens openings used for exposure.

The first optical image and the second optical image are stored, for example, in the defect information storage unit 637. The lithography simulator 2000 reads the first optical image or the second optical image via the interface 800 and can be used to create the space transfer image.

Next, the lithography simulator 2000 creates a reference transfer image based on a first or second reference image by using the transfer image creation unit 2010 (S72).

Next, the lithography simulator 2000 performs a third comparison between the space transfer image and the reference transfer image by using the transfer image comparison unit 2020 (S74).

Next, the lithography simulator 2000 determines based on the third comparison by using the transfer image determination unit 2030 whether a first defect needs to be corrected (S76).

Hereinafter, an effect of the present embodiment will be described.

Generally, a predetermined algorithm and a predetermined threshold referred to in defect determination are appropriately set so as to detect a target defect before an inspection by using a sensitivity evaluation mask. However, a pattern is increasingly refined, and as an optical proximity correction (OPC) technique is frequently used, a target defect may not be detected in the setting by the above-described sensitivity evaluation mask. As one of methods to solve this issue, there is a method for detecting a defect by using an algorithm and a threshold having higher defect detection sensitivity than the predetermined algorithm and the predetermined threshold, which are set by the sensitivity evaluation mask. In this case, many defects (nuisance defects) are detected which do not cause a problem when a pattern is transferred on a wafer. Therefore, there are problems that a reviewing time in an inspection time is increased, and a large capacity storage apparatus is required to store defect information.

In the embodiment, the number of first defects in the first portion is calculated as a defect total number. In the case where the defect total number is larger than a defect number threshold, a second defect determination threshold increased by a predetermined amount from a first defect determination threshold is calculated. Specifically, when the defect total number becomes too large, the defect determination threshold is changed. Further, a defect determination algorithm which can decrease the number of detected defects in comparison with a first defect determination algorithm is used in an inspection of the second portion 20 as a second defect determination algorithm. Accordingly, an increase in an inspection time and a reviewing time and an increase in size of the defect information storage unit 637 can be prevented.

In addition, in the embodiment, in the case where the second defect determination threshold is larger than a limit defect determination threshold, the second defect determination threshold is equalized with the limit defect determination threshold. Accordingly, when a defect determination threshold becomes too large, a possibility that a defect causing a problem is not detected is increased. Therefore, a maximum defect determination threshold can be set as a limit defect determination threshold. Accordingly, an inspection without fail becomes possible.

Further, in the embodiments, the second defect determination threshold increased by the predetermined amount from the first defect determination threshold is calculated in the case where the defect total number is larger than the defect number threshold, and in the case where the defect total number is equal to or less than the defect number threshold, the second defect determination threshold is equalized with the first defect determination threshold. Then, a lighting light is irradiated to the second portion of a sample to be inspected. A third optical image in which a lighting light transmitted through the second portion is imaged or a fourth optical image in which the lighting light reflected by the second portion is imaged is obtained. A third comparison between a third reference image referred to the third optical image and the third optical image or a fourth comparison between a fourth reference image referred to a fourth optical image and the fourth optical image is performed based on the second defect determination threshold. It is determined whether the second portion includes a second defect. In the case where the second portion is determined to have the second defect, a second coordinate of the second defect, the second defect determination threshold, the third or fourth optical image, and the third or fourth reference image are stored. The number of second defects in the second portion is calculated. The defect total number is calculated by adding the number of first defects and the number of second defects. In the case where the defect total number is larger than the defect number threshold, a third defect determination threshold increased by the predetermined amount from the second defect determination threshold is calculated. In the case where the defect total number is equal to or less than the defect number threshold, the third defect determination threshold is equalized with the second defect determination threshold. Thus, for example, in the embodiment, in the case where the defect total number is larger than the defect number threshold in the first portion, an inspection by using a large defect determination threshold is possible in the second to sixth portions. Accordingly, the number of defects excessively detected can be decreased, and an increase in an inspection time and a reviewing time can be prevented. Further, the number of optical images and reference images which are stored in the defect information storage unit can be decreased, and an increase in size of the defect information storage unit 637 can be prevented.

The inspection apparatus 1000 according to the embodiment further includes the lithography simulator 2000. By creating a space transfer image, the inspection apparatus 1000 can detect a defect and determine necessity of a correction of the defect. Accordingly, if a defect determined to be defective in a mask is a nuisance defect which does not become a problem when being transferred on a wafer, an inspection method in which the defect is not detected can be performed. Therefore, an increase in the number of defects excessively detected, an increase in an inspection time and a reviewing time, and an increase in size of the defect information storage unit 637 can be further prevented.

As described above, according to the embodiment, an inspection apparatus and an inspection method which can prevent an increase in the number of defects excessively detected and an increase in an inspection time can be provided by: irradiating a first portion of a sample to be inspected with a lighting light; obtaining a first optical image in which the lighting light transmitted through the first portion is imaged or a second optical image in which the lighting light reflected by the first portion is imaged; performing, based on a first defect determination threshold, a first comparison between a first reference image referred to the first optical image and the first optical image or a second comparison between a second reference image referred to the second optical image and the second optical image; determining whether the first portion includes a first defect; storing a first coordinate of the first defect, the first defect determination threshold, the first or second optical image, and the first or second reference image in the case where it is determined that the first portion includes the first defect; calculating the number of first defects in the first portion as a defect total number; calculating a second defect determination threshold increased by a predetermined amount from the first defect determination threshold in the case where the defect total number is larger than a defect number threshold; and equalizing the second defect determination threshold with the first defect determination threshold in the case where the defect total number is equal to or less than the defect number threshold.

In the above description, process contents or operation contents of "the control unit", "the comparison unit", "the reference unit", "the pattern generation unit", "the position detection unit," "the determination unit", "the transfer image comparison unit", "the transfer image creation unit", "the transfer image comparison unit", and "the transfer image determination unit" can be configured by a program operable by a computer. Alternatively, in addition to a program being software, the program may be performed by hardware or by combining software and hardware. Alternatively, firmware may be combined. In addition, in the case where the contents are included in a program, the program is stored in a storage medium in a magnetic disc unit, a magnetic tape unit, a FD, a read-only memory (ROM), and a solid state drive (SSD), which are not illustrated. Further, the storage units including "the pattern data storage unit", "the defect determination threshold storage unit", "the limit defect determination threshold storage unit", "the defect number threshold storage unit, "The defect information storage unit", "the defect total number storage unit", and "the defect determination algorithm storage unit" include a storage medium, such as a magnetic disk unit, a magnetic tape unit, a FD, a read-only memory (ROM), and a solid state drive (SSD).

In the above-described description, by performing S10 to S52 in accordance with a flowchart illustrated in FIG. 3, both of the first portion 10 and the second portion 20 are inspected. However, for example, first, the first portion 10 is inspected, and when it is clarified in S26 that the second defect determination threshold increased by a predetermined amount from the first defect determination threshold is calculated, the process is returned to the previous step from S26. The first portion 10 is again inspected after the first defect determination threshold is increased, and then the second portion 20 may be inspected.

The description regarding a portion which is not directly needed in a description of the present disclosure, such as a configuration, is omitted in the embodiments. However, a necessary configuration can be selected appropriately for use. Further, all of inspection apparatuses and inspection methods which include elements in the present disclosure and can be appropriately changed in design by a person skilled in the art are included in the scope of the present disclosure. The scope of the present disclosure is defined by the scope of claims and the equivalent scope thereof.

What is claimed is:

1. An inspection method, comprising:
   irradiating a first portion of a sample to be inspected with a lighting light;
   obtaining a first optical image in which the lighting light transmitted through the first portion is imaged or a second optical image in which the lighting light reflected by the first portion is imaged;
   performing, based on a first defect determination threshold, a first comparison between a first reference image and the first optical image or a second comparison between a second reference image and the second optical image;
   determining whether the first portion includes a first defect;
   storing a first coordinate of the first defect, the first defect determination threshold, the first or second optical image, and the first or second reference image in a case where it is determined that the first portion includes the first defect;
   calculating the number of first defects in the first portion as a defect total number;
   calculating a second defect determination threshold increased by a predetermined amount from the first defect determination threshold in a case where the defect total number is larger than a defect number threshold; and
   equalizing the second defect determination threshold with the first defect determination threshold in a case where the defect total number is equal to or less than the defect number threshold.

2. The inspection method according to claim 1, comprising equalizing the second defect determination threshold with the first defect determination threshold in a case where the first portion does not have the first defect.

3. The inspection method according to claim 1, comprising calculating the second defect determination threshold increased by the predetermined amount from the first defect determination threshold in a case where the defect total number is larger than the defect number threshold, and equalizing the second defect determination threshold with a limit defect determination threshold in a case where the second defect determination threshold is larger than the limit defect determination threshold.

4. The inspection method according to claim 1, comprising:

calculating the second defect determination threshold increased by the predetermined amount from the first defect determination threshold in a case where the defect total number is larger than the defect number threshold; and equalizing the second defect determination threshold with the first defect determination threshold in a case where the defect total number is equal to or less than the defect number threshold, the inspection method, then comprising:

irradiating a second portion of the sample to be inspected with a lighting light;

obtaining a third optical image in which the lighting light transmitted through the second portion is imaged or a fourth optical image in which the lighting light reflected by the second portion is imaged;

performing, based on the second defect determination threshold, a third comparison between a third reference image and the third optical image or a fourth comparison between a fourth reference image and the fourth optical image;

determining whether the second portion includes a second defect;

in a case where it is determined that the second portion includes the second defect, storing a second coordinate of the second defect, the second defect determination threshold, the third or fourth optical image, and the third or fourth reference image;

calculating the number of second defects in the second portion;

calculating the defect total number by adding the number of first defects and the number of second defects;

in a case where the defect total number is larger than the defect number threshold, calculating a third defect determination threshold increased by the predetermined amount from the second defect determination threshold; and in a case where the defect total number is equal to or less than the defect number threshold, equalizing the third defect determination threshold with the second defect determination threshold.

5. The inspection method according to claim 4, comprising:

determining by using a first defect determination algorithm whether the first portion includes the first defect; and determining by using a second defect determination algorithm different from the first defect determination algorithm whether the second portion includes the second defect.

6. The inspection method according to claim 5, wherein a pattern provided in the first portion and a pattern provided in the second portion are different.

7. The inspection method according to claim 4, comprising equalizing the third defect determination threshold with the second defect determination threshold in a case where it is determined that the second portion does not have the second defect.

8. The inspection method according to claim 1, comprising:

in a case where the defect total number is larger than the defect number threshold, calculating the second defect determination threshold increased by the predetermined amount from the first defect determination threshold; and in a case where the defect total number is equal to or less than the defect number threshold, equalizing the second defect determination threshold with the first defect determination threshold, the inspection method, then comprising:

creating a space transfer image based on the first or second optical image;

creating a reference transfer image based on the first or second reference image;

performing a third comparison between the space transfer image and the reference transfer image; and determining based on the third comparison whether the first defect needs correction.

9. An inspection apparatus, comprising:

an irradiation circuit configured to irradiate a first portion of a sample to be inspected with a lighting light;

an imaging circuit configured to obtain a first optical image in which the lighting light transmitted through the first portion is imaged or a second optical image in which the lighting light reflected by the first portion is imaged;

a comparison circuit configured to, based on a first defect determination threshold, perform a first comparison between a first reference image and the first optical image or a second comparison between a second reference image and the second optical image;

a determination circuit configured to determine whether the first portion includes a first defect;

a defect determination threshold storage device configured to store the first defect determination threshold;

a defect information storage device configured to store a first coordinate of the first defect, the first defect determination threshold, the first or second optical image, and the first or second reference image;

a defect total number storage device configured to store the number of first defects in the first portion as a defect total number; and a defect number threshold storage device configured to store a defect number threshold.

10. The inspection apparatus according to claim 9, further comprising a defect determination algorithm storage device configured to store a defect determination algorithm to be used to determine whether the first portion includes the first defect.

11. An inspection system, comprising the inspection apparatus according to claim 9 and a lithography simulator, the lithography simulator comprising:

a transfer image creation circuit configured to create a space transfer image based on the first or second optical image and create a reference transfer image based on the first or second reference image;

a transfer image comparison circuit configured to perform a third comparison between the space transfer image and the reference transfer image; and a transfer image determination circuit configured to determine based on the third comparison whether the first defect needs to be corrected.

* * * * *